US010201285B2

(12) United States Patent
Sawanoi et al.

(10) Patent No.: US 10,201,285 B2
(45) Date of Patent: Feb. 12, 2019

(54) BLOOD PRESSURE MEASUREMENT DEVICE INCLUDING WRAPPING STRENGTH EVALUATION CAPABILITIES

(71) Applicants: Yukiya Sawanoi, Nara (JP); Shingo Yamashita, Kyoto (JP); Toshiaki Yuasa, Moriyama (JP)

(72) Inventors: Yukiya Sawanoi, Nara (JP); Shingo Yamashita, Kyoto (JP); Toshiaki Yuasa, Moriyama (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 1050 days.

(21) Appl. No.: 13/632,921

(22) Filed: Oct. 1, 2012

(65) Prior Publication Data

US 2013/0030310 A1 Jan. 31, 2013

Related U.S. Application Data

(63) Continuation of application No. PCT/JP2011/052764, filed on Feb. 9, 2011.

(30) Foreign Application Priority Data

Mar. 30, 2010 (JP) ................................. 2010-077984

(51) Int. Cl.
*A61B 5/02* (2006.01)
*A61B 5/022* (2006.01)
*A61B 5/021* (2006.01)

(52) U.S. Cl.
CPC ...... *A61B 5/02233* (2013.01); *A61B 5/02141* (2013.01)

(58) Field of Classification Search
CPC ..... A61B 5/021; A61B 5/022; A61B 5/02208; A61B 5/02225; A61B 5/024; A61B 5/02438
See application file for complete search history.

(56) References Cited

U.S. PATENT DOCUMENTS 4,889,132 A * 12/1989 Hutcheson ......... A61B 5/02208
600/481
6,336,044 B1 * 1/2002 Ghiassi ................ A61B 5/0059
250/316.1

(Continued)

FOREIGN PATENT DOCUMENTS

JP 63-189128 A 8/1988
JP 02-114934 A 4/1990

(Continued)

OTHER PUBLICATIONS

International Search Report issued in corresponding International Application No. PCT/JP2011/052764 dated May 17, 2011 and English translation thereof (2 pages).

(Continued)

*Primary Examiner* — Tiffany Weston
*Assistant Examiner* — Tho Tran
(74) *Attorney, Agent, or Firm* — Osha Liang LLP

(57) ABSTRACT

A cuff of a blood pressure measurement device compresses a measurement site by being wrapped therearound. A control unit evaluates the wrapping strength of the cuff, by comparing a detection amount detected based on the output of a sensor with a history of the detection amount stored in the storage unit.

7 Claims, 10 Drawing Sheets

(56) References Cited

U.S. PATENT DOCUMENTS

| | | | | |
|---|---|---|---|---|
| 7,611,468 B2* | 11/2009 | Inoue | ................... | A61B 5/021 600/490 |
| 2009/0312651 A1* | 12/2009 | Sano | ................ | A61B 5/02141 600/493 |
| 2011/0009756 A1* | 1/2011 | Merilainen | .................. | 600/490 |

FOREIGN PATENT DOCUMENTS

| | | |
|---|---|---|
| JP | 2005-305028 A | 11/2005 |
| JP | 2007-167171 A | 7/2007 |
| JP | 2008-188197 A | 8/2008 |
| WO | WO2008096741 A1 * | 8/2008 |

OTHER PUBLICATIONS

Patent Abstracts of Japan, Publication No. 2005-305028, Published on Nov. 4, 2005, 1 page.
Patent Abstracts of Japan, Publication No. 02-114934, Published on Apr. 27, 1990, 1 page.
Patent Abstracts of Japan, Publication No. 2008-188197, Published on Aug. 21, 2008, 1 page.
Patent Abstracts of Japan, Publication No. 2007-167171, Published on Jul. 5, 2007, 1 page.

* cited by examiner

BLOOD PRESSURE MEASUREMENT DEVICE INCLUDING WRAPPING STRENGTH EVALUATION CAPABILITIES

TECHNICAL FIELD

The present invention relates to a blood pressure measurement device, and more particularly to a blood pressure measurement device for wrapping a cuff around and compressing a measurement site when measuring blood pressure.

BACKGROUND ART

Blood pressure is one of the indices for analyzing circulatory diseases, and performing risk analysis based on blood pressure is effective in preventing cardiovascular diseases such as stroke, heart failure, and myocardial infarction, for example. Conventionally, diagnosis has been made using blood pressure measured at a medical institution during a hospital visit, health checkup or the like (casual blood pressure). However, research in recent years has found that blood pressure measured at home (home blood pressure) is more useful in diagnosing circulatory disease than casual blood pressure. This has lead to sphygmomanometers for home use becoming widespread, and there are said to be over 30 million in homes across Japan.

In order to measure blood pressure accurately with a blood pressure measurement device, the cuff needs to be appropriately wrapped around the measurement site such as the upper arm. However, with blood pressure measurement devices to date, it was difficult to determine whether the cuff was appropriately placed, and placement varied depending on the person, resulting in not being able to measure blood pressure accurately.

With respect to this, Patent Literature 1 (JP 2005-305028A), Patent Literature 2 (JP 02-114934A) and Patent Literature 3 (JP 2008-188197A), for example, disclose technologies for determining whether the strength with which the cuff is wrapped is appropriate, based on the amount of air sent to the cuff and the manner in which the cuff pressure increases at the start of blood pressure measurement, in the process of increasing the cuff pressure.

Patent Literature 1: JP 2005-305028A
Patent Literature 2: JP 02-114934A
Patent Literature 3: JP 2008-188197A

SUMMARY OF INVENTION

However, even if the same amount of air is sent to the cuff in the process of increasing cuff pressure such as described above, the manner in which the cuff pressure increases conceivably changes depending not only on the wrapping strength of the cuff, but also on the size (circumferential length) and the quality of the measurement site (hardness, etc.) around which the cuff is wrapped. Accordingly, with the technologies disclosed in Patent Literatures 1 to 3 that determine wrapping strength based only on the manner in which the cuff pressure increases, it is difficult to make the person being measured aware of variation in the wrapping strength when such variation occurs, because there is no simple way to compare the results of determining the wrapping strength each time measurement is performed.

Therefore, one or more embodiments of the present invention detect variation in the wrapping strength of the cuff when such variation occurs in a blood pressure measurement device, and make the person being measured aware of that fact.

A blood pressure measurement device according to one or more embodiments of the present invention is provided with a cuff that compresses a measurement site by being wrapped therearound, and includes a sensor that detects a behavior of the cuff and a control unit that detects a detection amount for an index of blood pressure based on an output of the sensor, the control unit measuring blood pressure based on the detection amount, the blood pressure measurement device further including a storage unit that stores a history of the detection amount detected by the control unit, and the control unit evaluating a wrapping strength of the cuff, by comparing the detection amount detected based on the output of the sensor with a history of the detection amount stored in the storage unit.

According to one or more embodiments of the present invention, the control unit detects an amount related to an amount of arterial volume change in the measurement site around which the cuff is wrapped.

According to one or more embodiments of the present invention, the control unit detects a pressure pulse wave amplitude of an artery in the measurement site around which the cuff is wrapped.

According to one or more embodiments of the present invention, the storage unit stores the history of the detection amount in association with a history of a blood pressure value measured based on the detection amount.

According to one or more embodiments of the present invention, the control unit evaluates the wrapping strength of the cuff around the measurement site, by comparing a maximum value of the detected detection amount and a maximum value in the history of the detection amount stored in the storage unit.

According to one or more embodiments of the present invention, the control unit evaluates the wrapping strength of the cuff around the measurement site, by comparing the detected detection amount with the detection amount corresponding to one or more blood pressure values out of a systolic blood pressure, an average blood pressure and a diastolic blood pressure of blood pressure values in each history of the detection amount stored in the storage unit.

According to one or more embodiments of the present invention, the control unit evaluates the wrapping strength of the cuff around the measurement site, by comparing a detection value of the detected detection amount with the detection amount corresponding to a representative value of measured blood pressure values based on the detection amount in each history of the detection amount stored in the detected storage unit.

According to one or more embodiments of the present invention, the detection amount is a volume of Korotkoff sounds of an artery in the measurement site around which the cuff is wrapped based on the output of the sensor.

According to one or more embodiments of the present invention, the wrapping strength of the cuff is evaluated. The person being measured is thereby able to recognize whether or not there is variation in the wrapping strength, based on the results of the evaluation.

DETAILED DESCRIPTION OF INVENTION

Hereinafter, embodiments of a blood pressure measurement device of the present invention will be described, with reference to the drawings. In the following description, the same reference signs are given to the same components and constituent elements. The names and functions thereof are also the same. Note that in the following embodiments the cuff is an air bladder and the measurement site around which the cuff is wrapped is assumed to be the upper arm, although the measurement site is not limited to the upper arm.

1. First Embodiment

A blood pressure measurement device that measures blood pressure in accordance with an oscillometric method is illustrated as a first embodiment of the blood pressure measurement device of the present invention.

1-1. External Configuration of Sphygmomanometer

Figure 1:
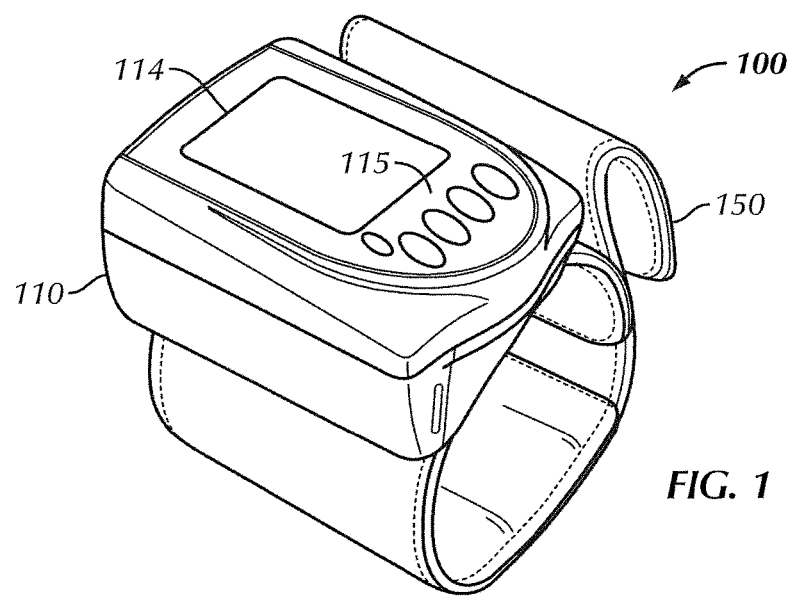
FIG. 1 is a diagram showing an external appearance of a sphygmomanometer 100 serving as a first embodiment of the blood pressure measurement device of the present invention.
Figure 2:
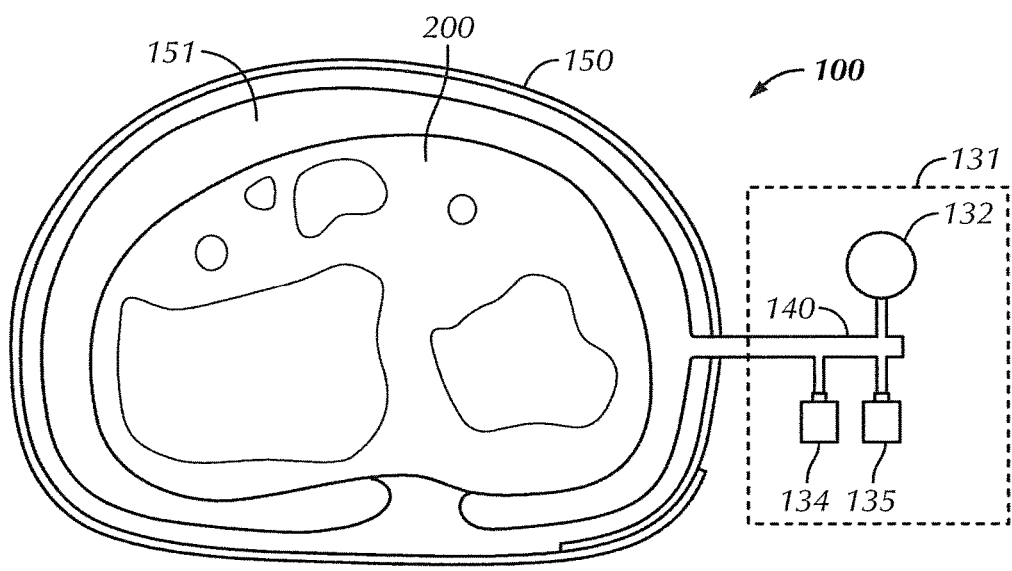
FIG. 2 is a diagram schematically showing a usage state of the sphygmomanometer of FIG. 1.

FIG. 1 shows an external appearance of a sphygmomanometer 100 serving as a first embodiment of the blood pressure measurement device of the present invention. FIG. 2 is a diagram schematically showing a usage state of the sphygmomanometer 100 of FIG. 1.

Referring to FIG. 1 and FIG. 2, the sphygmomanometer 100 is mainly provided with a device main body 110 and a cuff 150. In the case where the blood pressure measurement by the sphygmomanometer 100 is performed, the cuff 150 is wrapped around a measurement site 200.

The device main body 110 has a display unit 114 and an operation unit 115. The display unit 114 displays the results of measuring blood pressure values, pulse rates and so on using numerical values, graphs and the like in a manner that allows visible confirmation. A liquid crystal panel or the like, for example, may be used as this display unit 114. A power switch, a measurement switch and the like, for example, are arranged on the operation unit 115.

The cuff 150 is intended to be wrapped around the measurement site of the person being measured, and has a belt-like outer shape. The cuff 150 houses an air bladder 151 serving as a fluid bag for compressing the measurement site.

The cuff 150 and the device main body 110 are connected by an air tube 140 serving as a connecting tube. The air tube 140 consists of a flexible tube, one end of which is connected to an air system component for use in blood pressure measurement 131 that is provided in the device main body 110 and will be discussed later, and the other end of which is connected to the abovementioned air bladder 151 of the cuff 150.

1-2. Block Configuration of Sphygmomanometer

Figure 3:
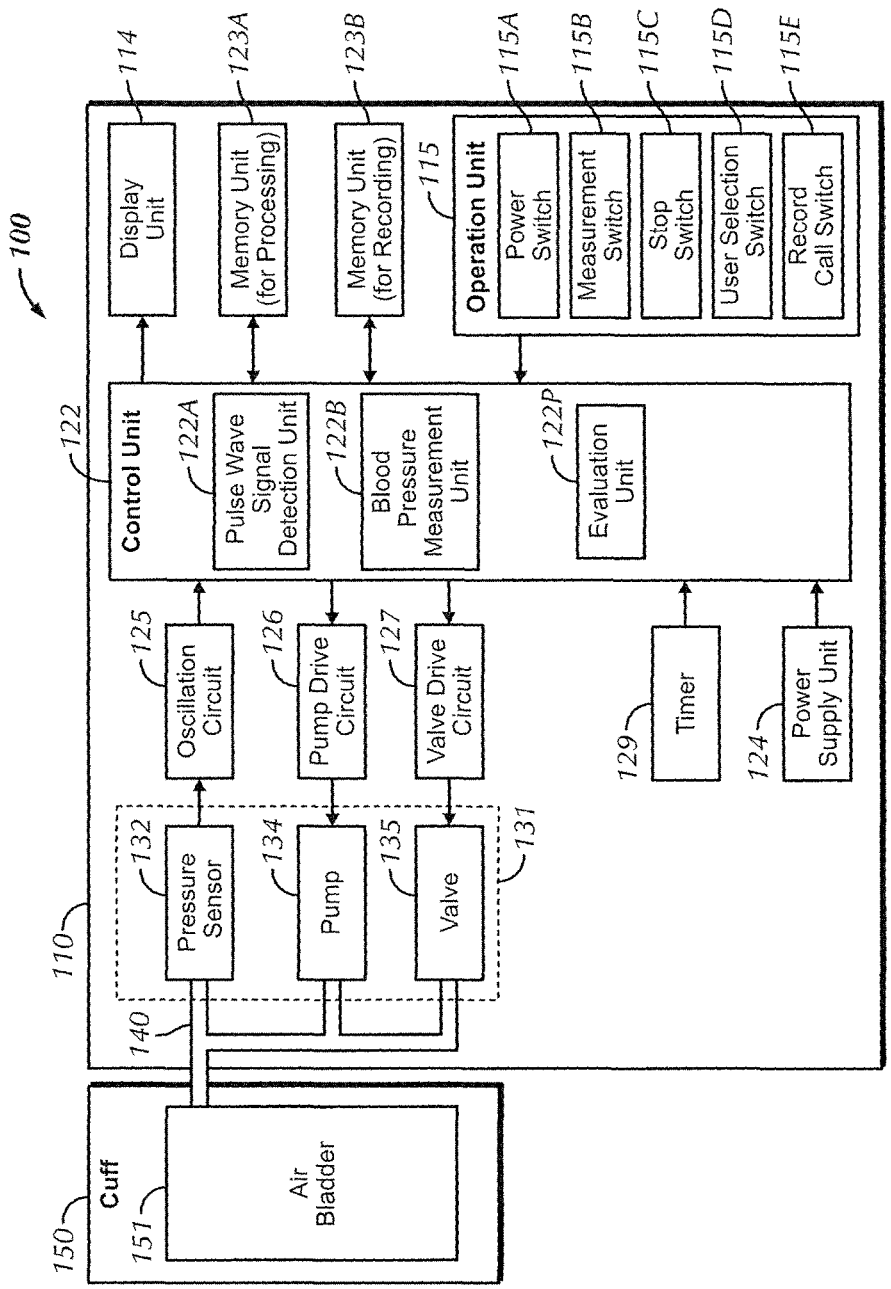
FIG. 3 is a functional block diagram showing a configuration of the sphygmomanometer of FIG. 1.

FIG. 3 is a functional block diagram showing a configuration of the sphygmomanometer 100.

Referring to FIG. 3, the air system component for use in blood pressure measurement 131 that is for supplying air to or discharging air from the air bladder 151 contained in the cuff 150 via the air tube 140 is provided inside the device main body 110 of the sphygmomanometer 100. A pressure sensor 132 that detects the pressure inside the air bladder 151, and a pump 134 and a valve 135 for expanding and contracting the air bladder 151 are included in the air system component for use in blood pressure measurement 131. Also, an oscillating circuit 125, a pump drive circuit 126 and a valve drive circuit 127 are provided inside the device main body 110 in relation to the air system component for use in blood pressure measurement 131.

In the present embodiment, a sensor that detects the behavior of the cuff 150 is constituted by the pressure sensor 132.

Furthermore, a control unit 122 for centrally controlling and monitoring the units, a memory unit 123A that stores a program for causing the control unit 122 to perform predetermined operations, a memory unit 123B for storing various information such as measured blood pressure values, a display unit 114 for displaying various information including blood pressure measurement results, the operation unit 115 that is operated in order to input various instructions for performing measurement, a timer 129 having a clock function, and a power supply unit 124 for supplying power to the control unit 122 and the functional blocks are installed in the device main body 110. The control unit 122 includes a processor such as a CPU (Central Processing Unit).

The memory unit 123A and the memory unit 123B are constituted by a storage medium. These memory units may be realized by a single storage medium or may be constituted by separate storage media. Exemplary storage media include media for storing programs in a non-volatile manner such as CD-ROM (Compact Disc-Read Only Memory), DVD-ROM (Digital Versatile Disk-Read Only Memory), USB (Universal Serial Bus) memory, memory card, FD (Flexible Disk), hard disk, magnetic tape, cassette tape, MO (Magnetic Optical Disc), MD (MiniDisc), IC (Integrated Circuit) card (excluding memory card), optical card, mask ROM, EPROM, and EEPROM (Electronically Erasable Programmable Read-Only Memory).

The pressure sensor 132 detects the pressure inside the air bladder 151 (hereinafter, "cuff pressure" as appropriate), and outputs a signal that depends on the detected pressure to the oscillation circuit 125. The pump 134 supplies air to the air bladder 151. The valve 135 opens and closes when maintaining the pressure inside the air bladder 151 and when discharging the air inside the air bladder 151. The oscillation circuit 125 outputs an oscillation frequency signal that depends on the output value of the pressure sensor 132 to the control unit 122. The pump drive circuit 126 controls the drive of the pump 134 based on a control signal provided from the control unit 122. The valve drive circuit 127 controls the opening and closing of the valve 135 based on a control signal provided from the control unit 122.

The control unit 122 includes a pulse wave signal detection unit 122A that detects arterial volume change superimposed on the cuff pressure as a pressure change (pressure pulse wave amplitude), by processing the signal output from the oscillation circuit 125, a blood pressure measurement unit 122B that measures blood pressure based on the pressure pulse wave amplitude detected by the pulse wave signal detection unit 122A, and an evaluation unit 122P that evaluates the wrapping strength of the cuff 150 in the measurement currently being performed by comparing the pressure pulse wave amplitude of the present measurement with the pressure pulse wave amplitude of past measurements. The evaluation unit 122P outputs an evaluation result by, for example, displaying the evaluation result on the display unit 114. An example of pressure pulse wave amplitude detected by the pulse wave signal detection unit 122A is shown in FIG. 4.

Figure 4:
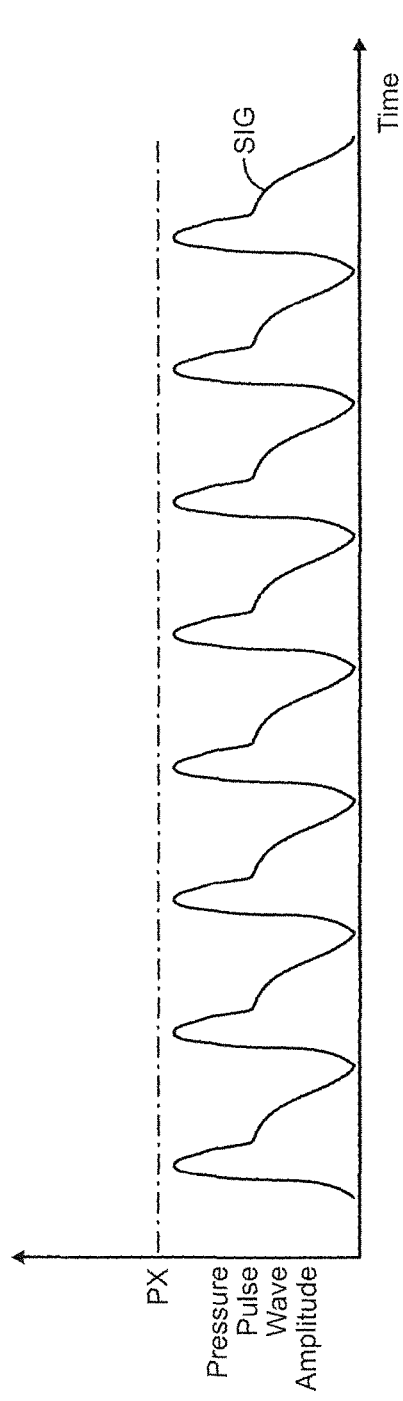
FIG. 4 is a diagram showing an example of pressure pulse wave amplitude detected by a pulse wave signal detection unit of FIG. 3.

The change in a pulse wave signal SIG over time is shown by FIG. 4. The pulse wave signal SIG of FIG. 4 indicates the change in the pulse wave when the cuff pressure is constant. The pulse wave signal SIG of FIG. 4 takes an amplitude PX as its maximum, and changes such that the same pattern is repeated every fixed period of time.

The operation unit 115 includes a power switch 115A for switching power supply to the sphygmomanometer 100 on and off, a measurement switch 115B that is operated when causing the sphygmomanometer 100 to start blood pressure measurement, a stop switch 115C that is operated in order to stop a blood pressure measurement operation currently being executed, a user selection switch 115D for selecting a person to be measured by the sphygmomanometer 100, and a record call switch 115E that is operated in order to display data such as blood pressure values, pulse rates and the like stored in the memory unit 123B on the display unit 114.

The results of measuring blood pressure values and pulse rates are stored in the memory unit 123B for each person that is measured. Stored measurement results are displayed on the display unit 114 in a manner that allows visible confirmation, using numerical values, graphs and the like, as a result of the record call switch 115E being operated.

1-3. Change in Pressure Pulse Wave Amplitude Following Change in Cuff Pressure

With the sphygmomanometer 100, the pressure pulse wave amplitude changes following a change in the cuff pressure. The change in pressure pulse wave amplitude following a change in cuff pressure is shown in (A) and (B) of FIG. 5.

Figure 5:
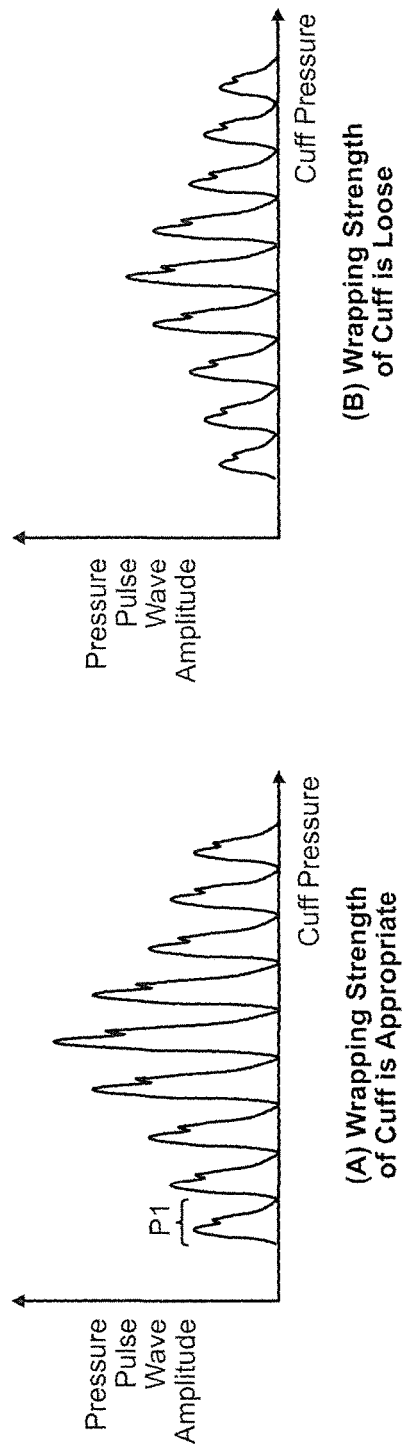
FIG. 5 is a diagram showing another example of pressure pulse wave amplitude detected by the pulse wave signal detection unit of FIG. 3.

First, referring to (A) of FIG. 5, the pressure pulse wave signal does not appear if the cuff pressure is less than a fixed value, and appears when the cuff pressure reaches the fixed value. Thereafter, following an increase in cuff pressure, the pressure pulse wave amplitude increases in value overall while repeating the fixed change pattern. Following an increase in cuff pressure after reaching a local maximum, the pressure pulse wave amplitude falls in value overall while repeating the fixed change pattern. When the cuff pressure is greater than or equal to a prescribed value, the pressure pulse wave amplitude will no longer be obtained. In (A) of FIG. 5, a single change pattern is indicated by P1.

With the sphygmomanometer 100, blood pressure measurement is performed based on the pressure pulse wave amplitude. Specifically, for example, in the process of reducing the cuff pressure that has been increased to exceed the above prescribed value, the cuff pressure at which the pressure pulse wave amplitude has increased rapidly is taken as the systolic blood pressure value, the cuff pressure at which the pressure pulse wave amplitude has decreased rapidly is taken as the diastolic blood pressure value, and the cuff pressure at which the pressure pulse wave amplitude presents a local maximum is taken as the average blood pressure value.

Pressure pulse wave amplitude in the case where the cuff pressure changes in the same range as (A) of FIG. 5 is shown in (B) of FIG. 5. Note that the state shown in (B) of FIG. 5 shows pressure pulse wave amplitude in the case where the wrapping of the cuff 150 around the measurement site is looser than the state shown in (A) of FIG. 5 (hereinafter, referred to as a "loose wrap" as appropriate). Note that (A) of FIG. 5 is assumed to show pressure pulse wave amplitude in the case where the cuff 150 is wrapped around the measurement site at an appropriate strength.

As compared with (A) of FIG. 5, the pressure pulse wave amplitude shown in (B) of FIG. 5 similarly tends to change relative to the change in cuff pressure, although the value of the amplitude is smaller overall than the pressure pulse wave amplitude shown in (A) of FIG. 5.

Note that in the case where wrapping of the cuff 150 around the measurement site is too tight, the value of the pressure pulse wave amplitude increases more overall than the case where the wrapping is appropriate. When the cuff 150 is, however, wrapped so tightly around the measurement site that blood has trouble flowing through the blood vessels, the value of the pressure pulse wave amplitude will be smaller than the case where the wrapping is appropriate.

In the present embodiment, the wrapping of the cuff 150 around the measurement site is evaluated, based on the values of pressure pulse wave amplitudes corresponding to the same cuff pressure (or cuff pressures showing the same characteristics such as systolic blood pressure value, diastolic blood pressure value, average blood pressure value, etc.) for a plurality of measurements.

1-4. Storage Mode of Pressure Pulse Wave Amplitude

With the sphygmomanometer 100, blood pressure values and pressure pulse wave amplitude values obtained in past blood pressure measurements are stored in the memory unit 123B as histories for each person that is measured. An exemplary storage mode of these values is shown in Tables 1 and 2.

TABLE 1

Blood Pressure Value Data

| ID | Measurement Date-Time | User | Blood Pressure Value/Pulse Rate | Pressure Pulse Wave Amplitude Data |
|---|---|---|---|---|
| 1 | y1/m1/d1 h1:m1 | A | SYS1, DIA1, PLS1 | PulseWave1 |
| 2 | y2/m2/d2 h2:m2 | A | SYS2, DIA2, PLS2 | PulseWave2 |
| 3 | y3/m3/d3 h3:m3 | A | SYS3, DIA3, PLS3 | PulseWave3 |
| 4 | y4/m4/d4 h4:m4 | A | SYS4, DIA4, PLS4 | PulseWave4 |
| 5 | y5/m5/d5 h5:m5 | A | SYS5, DIA5, PLS5 | PulseWave5 |
| ... | ... | | ... | ... |
| ... | ... | | ... | ... |
| ... | ... | | ... | ... |

TABLE 2

Pressure Pulse Wave Amplitude Data (PulseWave1)

| Cuff Pressure (mmHg) | Pressure Pulse Wave Amplitude (mmHg) |
|---|---|
| 0 | 0.00 |
| 5 | 0.01 |
| ... | ... |
| 85 | 2.20 |
| ... | ... |
| 180 | 0.01 |
| 176 | 0.02 |
| ... | ... |
| 0 | 0.00 |

In the blood pressure value data shown as Table 1, IDs specifying sets of data, measurement date-time, information specifying the person that is measured (user), blood pressure values, pulse rates, and information specifying pressure pulse wave amplitude data stored separately (pressure pulse wave amplitude data) are stored in association with each other. Here, systolic blood pressure value, diastolic blood pressure value or average blood pressure value, for example, may be stored as the blood pressure, and the cuff pressure when the pressure pulse wave amplitude takes its maximum may also be stored as the blood pressure value.

In the pressure pulse wave amplitude data shown as Table 2, the change pattern of pressure pulse wave amplitude such as shown with reference to (A) and (B) of FIG. 5 for a plurality of predetermined cuff pressures is shown.

In the example shown in Table 2, the pressure pulse wave amplitude data includes pressure pulse wave amplitudes for a plurality of cuff pressures (blood pressures). Note that in the present embodiment, it is sufficient if at least the pressure pulse wave amplitudes used at the time of "wrapping strength evaluation" in blood pressure measurement processing, which will be discussed later, are included in the pressure pulse wave amplitude data. In other words, for example, in the case where, in wrapping strength evaluation, the pressure pulse wave amplitudes corresponding to systolic blood pressure values obtained in the current blood pressure measurement are compared with pressure pulse wave amplitudes corresponding to systolic blood pressure values stored as histories, it is sufficient if at least the pressure pulse wave amplitudes corresponding to systolic blood pressure values for each measurement are stored in the pressure pulse wave amplitude data. Also, in the case where, in wrapping strength evaluation, the maximum values of pressure pulse wave amplitudes stored as histories are compared with the maximum value of the pressure pulse wave amplitude obtained with the current blood pressure measurement, it is sufficient if at least the maximum value of the pressure pulse wave amplitude for each measurement is stored in the pressure pulse wave amplitude data.

Information identifying each piece of pressure pulse wave amplitude data, such as "PulseWave1" in Table 2, is given to the pressure pulse wave amplitude data of each measurement.

1-5. Blood Pressure Measurement Processing

Figure 6:
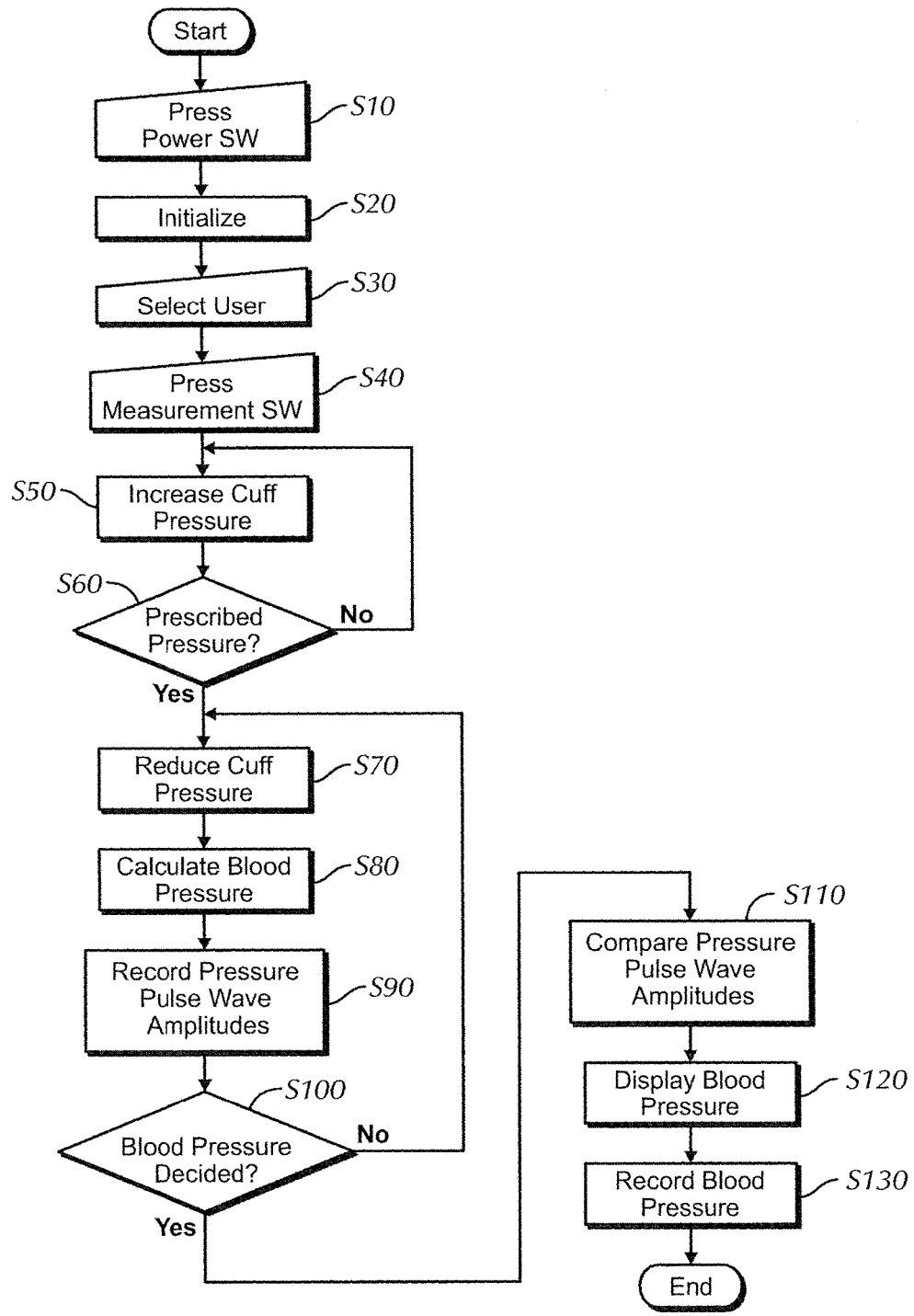
FIG. 6 is a flowchart of blood pressure measurement processing executed in the sphygmomanometer of FIG. 1.

FIG. 6 is a flowchart of blood pressure measurement processing executed in the sphygmomanometer 100. In the sphygmomanometer 100, this processing is realized by the control unit 122 executing a program stored in the memory unit 123A (or in a recording medium detachable from the device main body 110).

Referring to FIG. 6, in the blood pressure measurement processing, first at step S10, the control unit 122 stands by until the power switch 115A is operated, and advances the processing to step S20 when it is judged that the power switch 115A has been operated.

At step S20, the control unit 122 initializes the sphygmomanometer 100. The internal pressure of the air bladder 151 of the cuff 150 is thereby initialized.

Next, the control unit 122, at step S30, receives input of information selecting a user as a result of the user selection switch 115D being operated. If it is judged that information selecting a user has been input, the control unit 122 advances the processing to step S40. Note that at step S30, the control unit 122 generates a new ID for the blood pressure value data shown in Table 1, and secures a storage area for the new ID. The date-time acquired from the timer 129 at that point in time is then stored as the measurement date-time associated with the new ID, and information on the user for whom the input of information was received at step S30 is stored as the user associated with the new ID.

At step S40, the control unit 122 stands by until the measurement switch 115B is operated. When it is judged that the measurement switch 115B has been operated, the control unit 122 advances the processing to step S50.

At step S50, the control unit 122 causes the cuff pressure to be increased by causing the pump 134 to send air to the air bladder 151, and advances the processing to step S60.

At step S60, the control unit 122 judges whether the cuff pressure has reached a prescribed pressure, based on the output signal of the pressure sensor 132. The control unit 122 returns the processing to step S50 when it is judged that the prescribed pressure has not yet been reached, and advanced the processing to step S70 when it is judged that the prescribed pressure has been reached.

At step S70, the control unit 122 decreases the cuff pressure gradually by controlling the closed valve 135 to gradually open. The control unit 122, based on the pressure pulse wave signal superimposed on the signal detected by the pressure sensor 132 following this depressurization process, calculates blood pressure (systolic blood pressure and diastolic blood pressure) based on a prescribed procedure at step S80, and, at step S90, the control unit 122 causes the memory unit 123B to store the pressure pulse wave amplitude at that point in time, and advances the processing to step S100. The pressure pulse wave amplitude stored in step S90 is equivalent to the value of the pressure pulse wave amplitude relative to the cuff pressure at that point in time in the pressure pulse wave amplitude data (see Table 2) shown in Table 2.

At step S100, the control unit 122 judges whether the blood pressure calculation has been completed, and, when it is judged to have been completed (YES at step S100), advances the processing to step S110. On the other hand, if it is judged not to have been completed, the processing is returned to step S70.

At step S110, the control unit 122 compares the value of the pressure pulse wave amplitude obtained as a result of the current measurement with pressure pulse wave amplitude values obtained as a result of previous measurements and stored in the memory unit 123B, generates information evaluating the wrapping strength of the cuff 150 of the current measurement based on the comparison result, and advances the processing to step S120. The modes of comparison and evaluation referred to here will be discussed later.

At step S120, the control unit 122 causes the display unit 114 to display the blood pressure values acquired at step S80 together with the evaluation information generated at step S110, and advances the processing to step S130.

At step S130, the blood pressure values (systolic blood pressure value, diastolic blood pressure value and/or average blood pressure value) decided at step S80 and displayed on the display unit 114 at step S120 are stored in the blood pressure value data (Table 1), and the measurement processing is ended.

Note that the obtained blood pressure values are associated with the user selected at step S30, and stored in the memory unit 123.

Also, the control unit 122 controls the valve 135 so as to open fully at the same time as (or after) the display of blood pressure values at step S120, and releases the air in the air bladder 151.

1-6. Wrapping Strength Evaluation

The wrapping strength evaluation in step S110 will be described.

The control unit 122 first reads a value of the pressure pulse wave amplitude corresponding to the blood pressure value obtained with the current blood pressure measurement as a first value. The blood pressure value referred to here may be the systolic blood pressure value, the diastolic blood pressure value or the average blood pressure value, for example, and may also be the cuff pressure when the pressure pulse wave amplitude takes its maximum value.

Next, with regard to the blood pressure measurement to date, a pressure pulse wave amplitude value stored in Table 2 in the memory unit 123B in association with the person being measured for whom information was input to Table 1 at step S30 is read as a second value.

Note that as for the value read here as the second value, in the case where a value corresponding to the systolic blood pressure value is read as the value of the pressure pulse wave amplitude obtained with the current blood pressure measurement, the value of the pressure pulse wave amplitude similarly corresponding to the systolic blood pressure value is also read as the value of the blood pressure measurement to date. In the case where a value corresponding to the diastolic blood pressure value is read, the value of the pressure pulse wave amplitude similarly corresponding to the diastolic blood pressure value is also read as the value of the blood pressure measurement to date. In the case where a value corresponding to the average blood pressure value is read, the value of the pressure pulse wave amplitude similarly corresponding to the average blood pressure value is also read as the value of the blood pressure measurement to date.

Also, the value read as the second value is the pressure pulse wave amplitude corresponding to the systolic blood pressure value or the like, and may be the immediately previous measurement result for the person being measured for whom information was input at step S30, or may be a representative value such as the average value, minimum value or maximum value of a prescribed number (e.g., 5) of most recent measurement results.

The control unit 122 then calculates the difference between the first value and the second value (second value−first value), and evaluates the wrapping strength based on the value of this difference REF. For example, the wrapping strength is evaluated as being appropriate if REF is less than or equal to "A", tight if REF exceeds "A", and loose if REF is less than "−A".

Also, wrapping strength may be evaluated across multiple levels. An example will be described in which wrapping strength is evaluated across seven levels, for example. The wrapping strength is evaluated as being appropriate if REF is less than or equal to "A1", slightly tight if REF exceeds "A1" and is less than or equal to "A2", tight if REF exceeds "A2" and is less than or equal to "A3", quite tight if REF exceeds "A3", slightly loose if REF is less than "−A1" but greater than or equal to "−A2", loose if REF is less than "−A2" but greater than or equal to "−A3", and quite loose if REF is less than "−A3". Note that in this case A1 to A3 are positive numbers, where A1<A2<A3.

1-7. Exemplary Display of Wrapping Strength Evaluation Result

Figure 7:
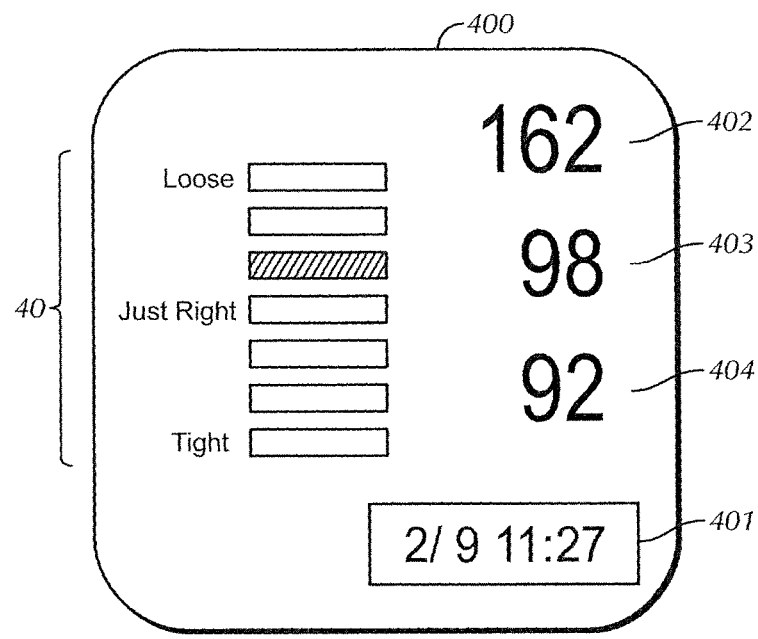
FIG. 7 is a diagram showing an exemplary screen displayed on a display unit of FIG. 1.

An exemplary screen displayed on the display unit 114 in step S120 is shown in FIG. 7.

Referring to FIG. 7, a systolic blood pressure value 402 (numerical value "162"), a diastolic blood pressure value 403 (numerical value "98"), a pulse value 404 (numerical value "92"), a current date-time 401, and an evaluation display portion 40 consisting of a plurality of blocks are displayed on a screen 400.

The evaluation display portion 40 includes seven blocks corresponding to seven levels of evaluation such as described above. The block corresponding to the evaluation result out of the seven blocks is displayed in a different mode from the other blocks (shaded block in FIG. 7). Note that in FIG. 7 the block one up from the middle is displayed in a different mode and the evaluation result "slightly loose" is shown.

In the present embodiment described above, a detection amount for an index of blood pressure detected based on the output of a sensor (pressure sensor 132) is constituted by the pressure pulse wave amplitude utilized to evaluate the wrapping strength. Also, the pressure pulse wave amplitude is also information related to the amount of arterial volume change.

Also, in the present embodiment, a first storage unit and a second storage unit are constituted by the memory unit 123B that stores blood pressure value data (Table 1) and pressure pulse wave amplitude data (Table 2). Specifically, the second storage unit is constituted by a portion in the memory unit 123B that stores data associated in blood pressure value data with the ID of measurement data relating to blood pressure measurement processing currently being executed. Also, the first storage unit is constituted by a portion in the memory unit 123B that stores data associated in blood pressure value data with the IDs of previous measurement data.

An evaluation unit according to one or more embodiments of the present invention is constituted by the evaluation unit 122P that evaluates the wrapping strength of the cuff 150 by comparing the pressure pulse wave amplitude in the current detection result and a pressure pulse wave amplitude stored as a history. Note that the evaluation unit 122P outputs the evaluation result to the display unit 114 as the evaluation display portion 40 in FIG. 7, for example.

2. Second Embodiment 2-1. Configuration of Sphygmomanometer

A sphygmomanometer 100 serving as an exemplary blood pressure measurement device of the present embodiment performs blood pressure measurement in accordance with Korotkoff sounds. A similar external configuration to the sphygmomanometer 100 of the first embodiment can be adopted.

Figure 8:
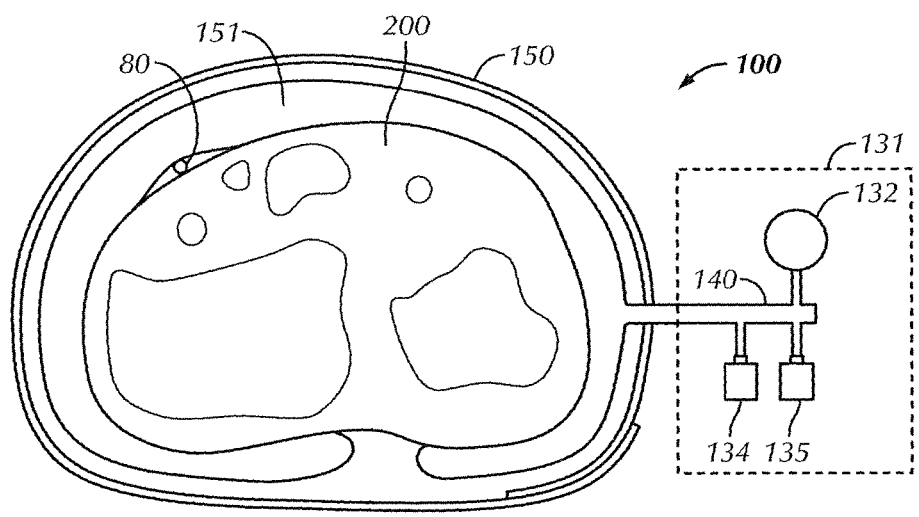
FIG. 8 is a diagram schematically showing a usage state of a sphygmomanometer serving as a second embodiment of the blood pressure measurement device of the present invention.
Figure 9:
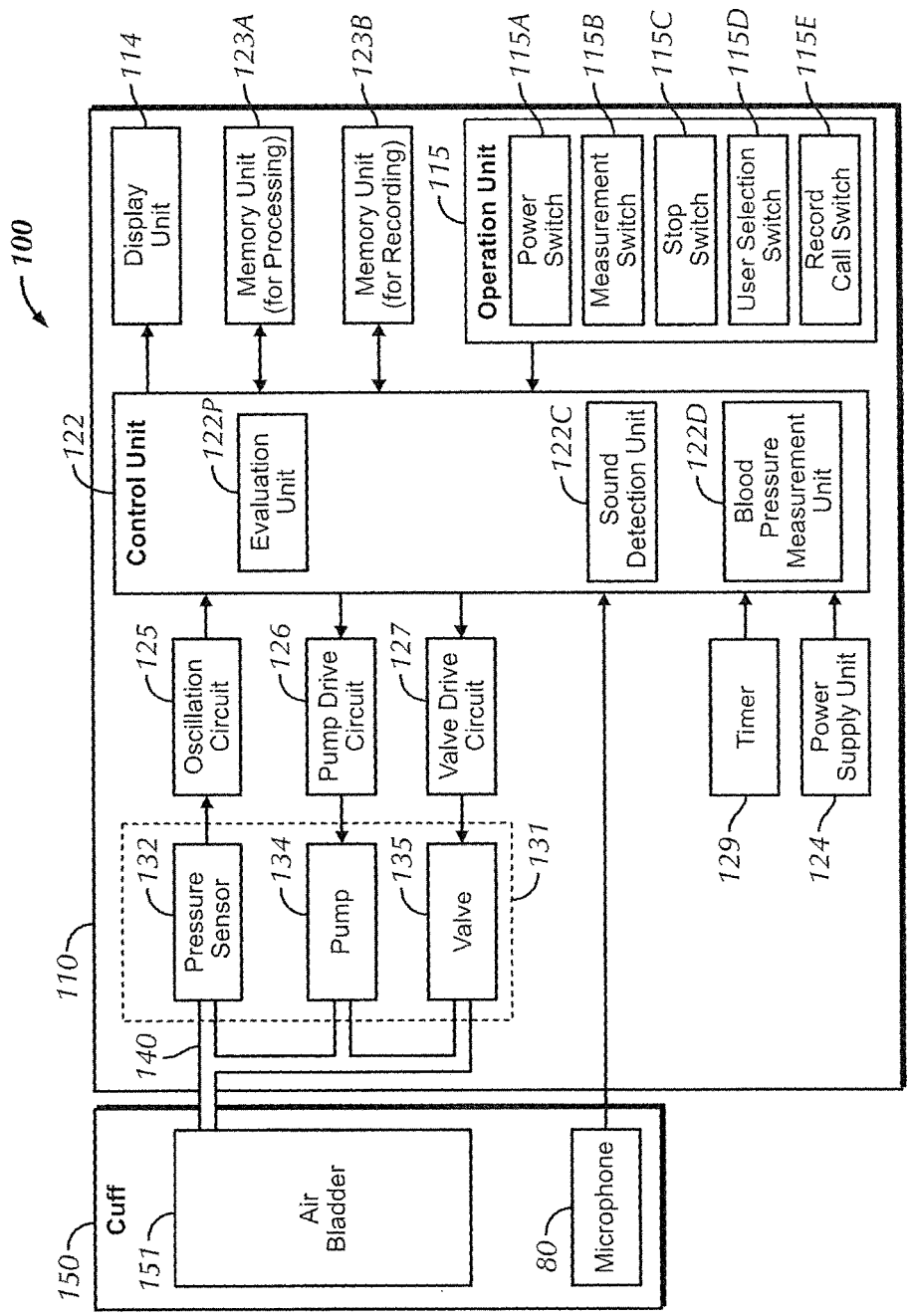
FIG. 9 is a functional block diagram showing a configuration of the sphygmomanometer of FIG. 8.

FIG. 8 is a diagram schematically showing a usage state of the sphygmomanometer 100 of the present embodiment, and FIG. 9 is a functional block diagram of the sphygmomanometer 100 of the present embodiment.

Referring to FIG. 8 and FIG. 9, in addition to the sphygmomanometer 100 of the first embodiment, the sphygmomanometer 100 of the present embodiment is further provided with a microphone 80 inside the cuff 150.

In the sphygmomanometer 100 of the present embodiment, the cuff 150 is wrapped around the measurement site 200, and Korotkoff sounds produced as a result of the artery within the measurement site 200 being constricted by the cuff 150 are detected with the microphone 80.

Also, in the present embodiment, the control unit 122 includes a sound detection unit 122C that detects sounds output by the microphone 80, and a blood pressure measurement unit 122D that performs blood pressure measurement based on the sounds detected by the sound detection unit 122C.

Note that because the blood pressure measurement performed in the sphygmomanometer 100 of the present embodiment in accordance with Korotkoff sounds utilizing sounds output by the microphone 80 can employ known technology, description thereof will not be repeated.

Figure 10:
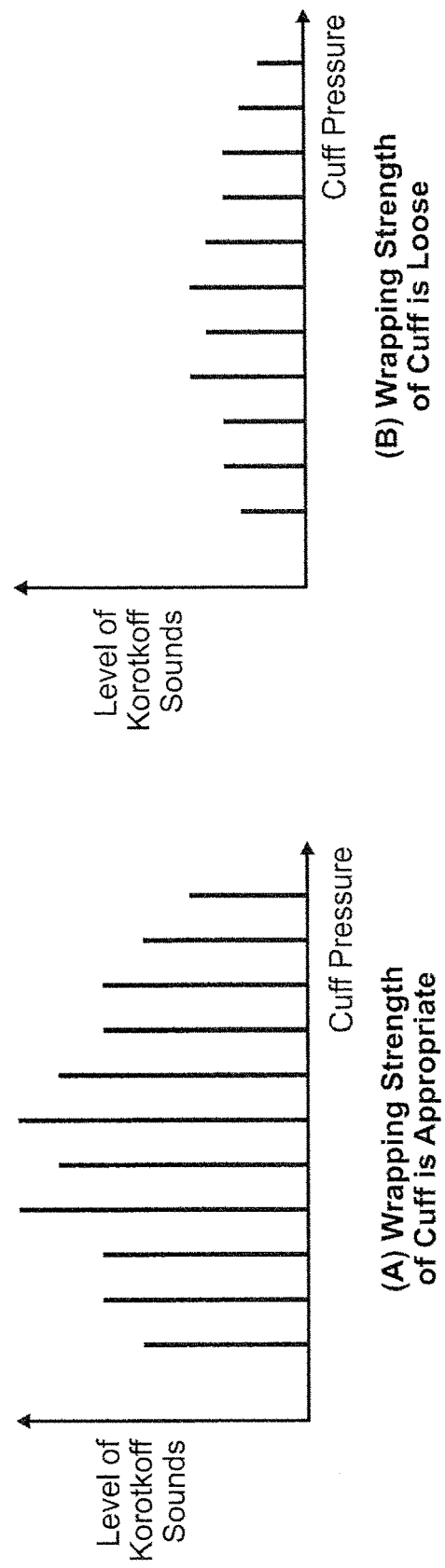
FIG. 10 is a diagram showing exemplary Korotkoff sounds detected by the sphygmomanometer of FIG. 8.

(A) of FIG. 10 shows changes in the volume (level) of Korotkoff sounds following changes in cuff pressure in the case where the wrapping strength of the cuff 150 is appropriate. (B) of FIG. 10 shows changes in the volume (level) of Korotkoff sounds following changes in cuff pressure in the case where the wrapping strength of the cuff 150 is loose.

Referring to (A) and (B) of FIG. 10, the level of Korotkoff sounds decreases overall when the cuff 150 is loosely wrapped.

Note that when the wrapping strength of the cuff 150 is tight, the level of Korotkoff sounds increases overall, as compared with the case where the wrapping strength is appropriate. When, however, the wrapping strength of the cuff 150 is so tight as to obstruct blood flow in the blood vessels, the level of Korotkoff sounds decreases overall, as compared with the case where the wrapping strength is appropriate.

2-2. Wrapping Strength Evaluation

The wrapping strength evaluation in step S110 (see FIG. 6) by the evaluation unit 122P of the sphygmomanometer 100 of the present embodiment will be described.

The control unit 122 first reads a level of Korotkoff sounds corresponding to the blood pressure value obtained with the current blood pressure measurement as a first value. The blood pressure value referred to here includes the systolic blood pressure value, the diastolic blood pressure value or the average blood pressure value, for example. The blood pressure value referred to here may also be the cuff pressure when the level of Korotkoff sounds takes its maximum.

Next, with regard to the blood pressure measurement to date, a level of Korotkoff sounds stored in Table 2 in the memory unit 123B in association with the person being measured for whom information was input to Table 1 at step S30 is read as a second value.

Note that as for the value read here as the second value, in the case where a value corresponding to the systolic blood pressure value is read as the level of Korotkoff sounds obtained with the current blood pressure measurement, the level of Korotkoff sounds similarly corresponding to the systolic blood pressure value is also read as the value of the blood pressure measurement to date. In the case where a value corresponding to the diastolic blood pressure value is read, the level of Korotkoff sounds similarly corresponding to the diastolic blood pressure value is also read as the value of the blood pressure measurement to date. In the case where a value corresponding to the average blood pressure value is read, the level of Korotkoff sounds similarly corresponding to an average blood pressure value is also read as the value of the blood pressure measurement to date.

Also, the value read as the second value is the level of Korotkoff sounds corresponding to the systolic blood pressure value or the like, and may be the immediately previous measurement result for the person being measured for whom information was input at step S30, or may be a representative value such as the average value, minimum value or maximum value of a prescribed number (e.g., 5 times) of most recent measurement results.

The control unit 122 then calculates the difference between the first value and the second value (second value−first value), and evaluates the wrapping strength based on the value of this difference REF01. For example, the wrapping strength is evaluated as being appropriate if REF01 is less than or equal to "B", tight if REF01 exceeds "B", and loose if REF01 is less than "−B".

Also, wrapping strength may be evaluated across multiple levels. An example will be described in which wrapping strength is evaluated across seven levels, for example. The wrapping strength is evaluated as being appropriate if REF01 is less than or equal to "B1", slightly tight if REF01 exceeds "B1" and is less than or equal to "B2", tight if REF01 exceeds "B2" and is less than or equal to "B3", quite tight if REF01 exceeds "B3", slightly loose if REF01 is less than "−B1" but greater than or equal to "−B2", loose if REF01 is less than "−B2" but greater than or equal to "−B3", and quite loose if REF01 is less than "−B3". Note that in this case B1 to B3 are positive numbers, where B1<B2<B3.

In the present embodiment described above, a sensor that detects the behavior of the cuff is constituted by the microphone 80.

An evaluation unit according to one or more embodiments of the present invention is constituted by the evaluation unit 122P that evaluates the wrapping strength of the cuff 150 by comparing Korotkoff sounds in the current detection result with Korotkoff sounds stored as a history. Note that the evaluation unit 122P outputs the evaluation result to the display unit 114 as the evaluation display portion 40 in FIG. 7, for example.

3. Third Embodiment 3-1. Configuration of Sphygmomanometer

A sphygmomanometer 100 serving as an exemplary blood pressure measurement device of the present embodiment performs blood pressure measurement by detecting arterial volume utilizing a photoelectric sensor including a light emitting element and a light receiving element. A similar external configuration to the sphygmomanometer 100 of the first embodiment can be adopted.

Figure 11:
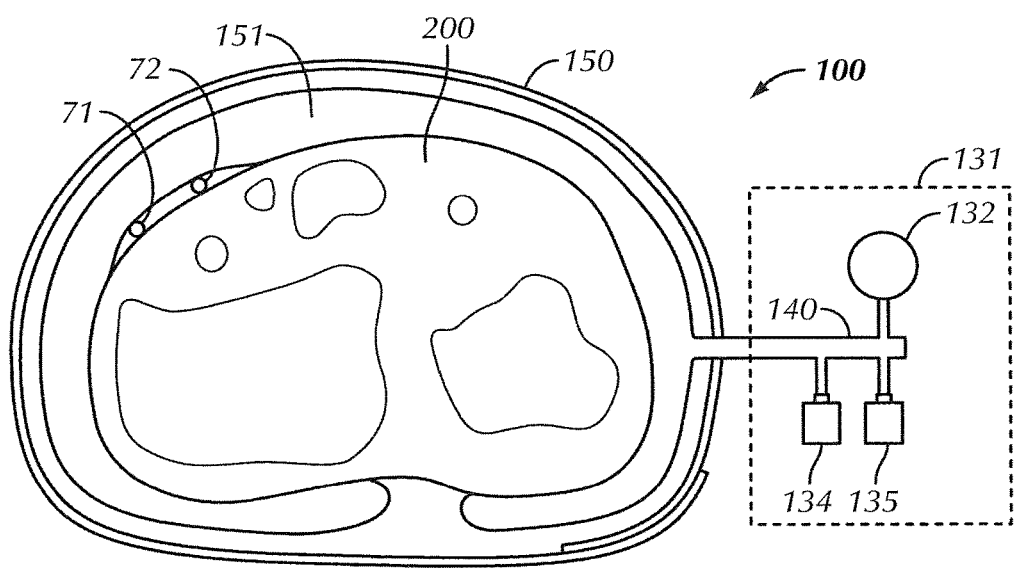
FIG. 11 is a diagram schematically showing a usage state of a sphygmomanometer serving as a third embodiment of the blood pressure measurement device of the present invention.
Figure 12:
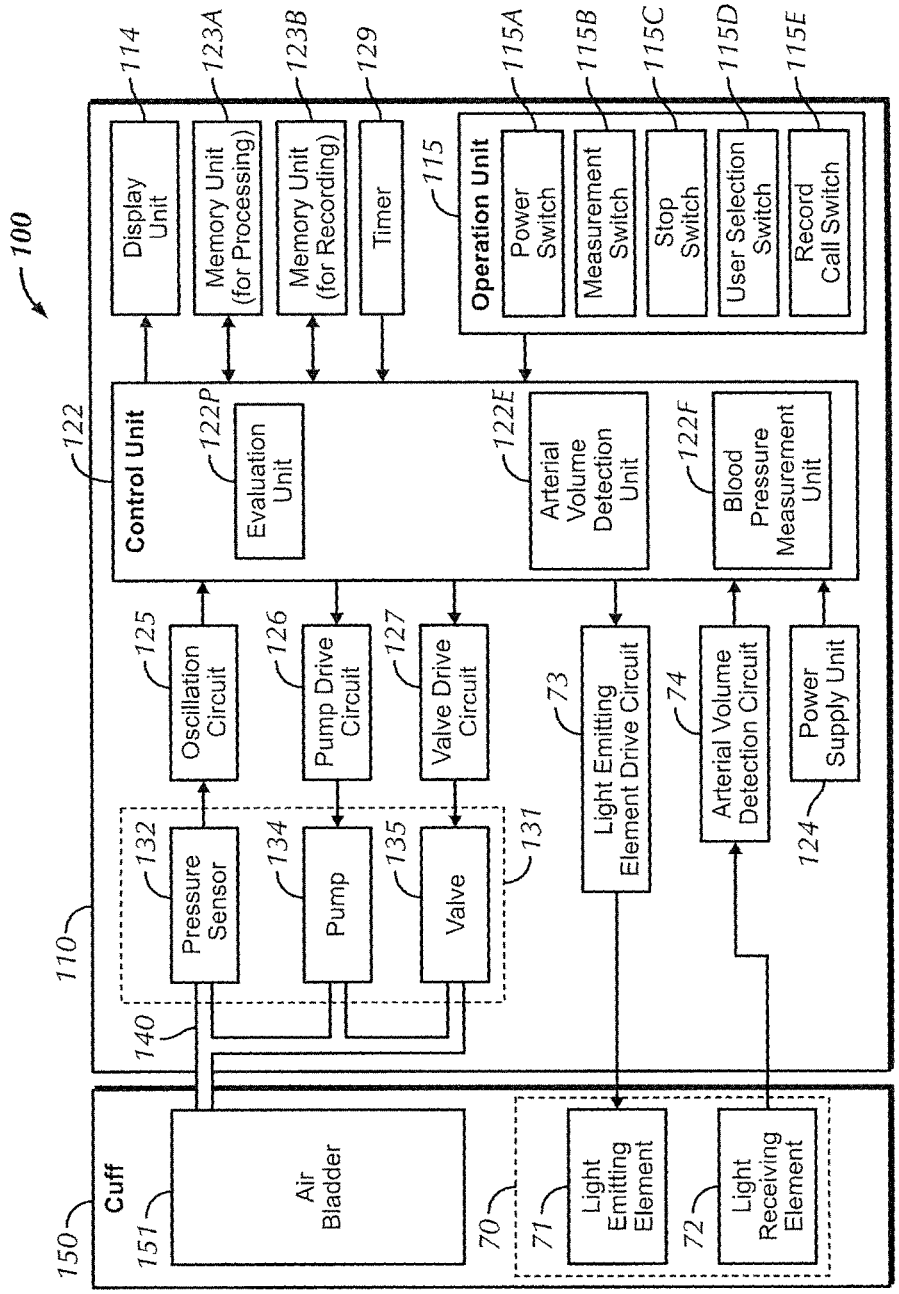
FIG. 12 is a functional block diagram showing a configuration of the sphygmomanometer of FIG. 11.

FIG. 11 is a diagram schematically showing a usage state of the sphygmomanometer 100 of the present embodiment, and FIG. 12 is a functional block diagram of the sphygmomanometer 100 of the present embodiment.

Referring to FIG. 11 and FIG. 12, in addition to the sphygmomanometer 100 of the first embodiment, the sphygmomanometer 100 of the present embodiment includes a photoelectric sensor 70 consisting of a light emitting element 71 and a light receiving element 72, a light emitting element drive circuit 73, and an arterial volume detection circuit 74. In the present embodiment, a sensor that detects the behavior of the cuff 150 is constituted by the photoelectric sensor 70.

Also, the control unit 122 includes an arterial volume detection unit 122E that detects arterial volume based on the output of the arterial volume detection circuit 74, and a blood pressure measurement unit 122F that measures blood pressure values based on the arterial volume detected by the arterial volume detection unit 122E.

The light emitting element 71 irradiates light toward a portion of the radial artery extending within the measurement site 200 (e.g., the wrist in the present embodiment), and is constituted by an LED (Light Emitting Diode), for example. The light receiving element 72 is a component that receives light irradiated by the light emitting element 71 that has passed through and/or been reflected by the radial artery, and is constituted by a PD (Photo Diode), for example.

In order to detect arterial volume accurately, according to one or more embodiments of the present invention, near-infrared light that readily passes through living body tissue is utilized as the detection light, and components capable of irradiating and receiving this near-infrared light are used as the light emitting element 71 and the light receiving element 72, respectively. More specifically, according to one or more embodiments of the present invention, near-infrared light near the wavelength of 940 nm is particularly used as the detection light irradiated from the light emitting element 71 and received with the light receiving element 72. Note that the detection light is not limited to near-infrared light near 940 nm, and light near the wavelength of 450 nm, light near the wavelength of 1100 nm, or the like can also be used.

The light emitting element drive circuit 73 is a circuit for causing the light emitting element 71 to emit light based on a control signal of the control unit 122, and causes the light emitting element 71 to emit light by applying a prescribed amount of current to the light emitting element 71. A direct current of around 50 mA, for example, is used as the current applied to the light emitting element 71. As for the light emitting element drive circuit 73, according to one or more embodiments of the present invention, a circuit that causes the light emitting element 71 to periodically emit pulsed light by supplying a pulse current with a prescribed duty cycle to the light emitting element 71 is utilized. Assuming that the light emitting element 71 is thus caused to emit pulsed light, it will be possible to suppress power applied to the light emitting element 71 per unit time, and to prevent the light emitting element 71 from heating up. Note that arterial volume can be detected more minutely by setting the drive frequency of the light emitting element 71 to a frequency (e.g., about 3 kHz) that is sufficiently higher than the frequency component (roughly 30 Hz) included in the variation in arterial volume to be detected.

The arterial volume detection circuit 74 is a circuit for generating a voltage signal according to the amount of received light based on the signal input from the light receiving element 72, and outputting the generated voltage signal to the control unit 122. Because the amount of light detected by the light receiving element 72 changes in proportion to arterial volume, the voltage signal generated with the arterial volume detection circuit 74 will also change in proportion to arterial volume, and the arterial volume will thereby be taken as the variation in voltage value. Here, the arterial volume detection circuit 74 includes processing circuits such as an analog filter circuit, a rectification circuit, an amplification circuit and an A/D (Analog/Digital) conversion circuit, for example, and outputs the signal input as an analog value as a digitized voltage signal.

Figure 13:
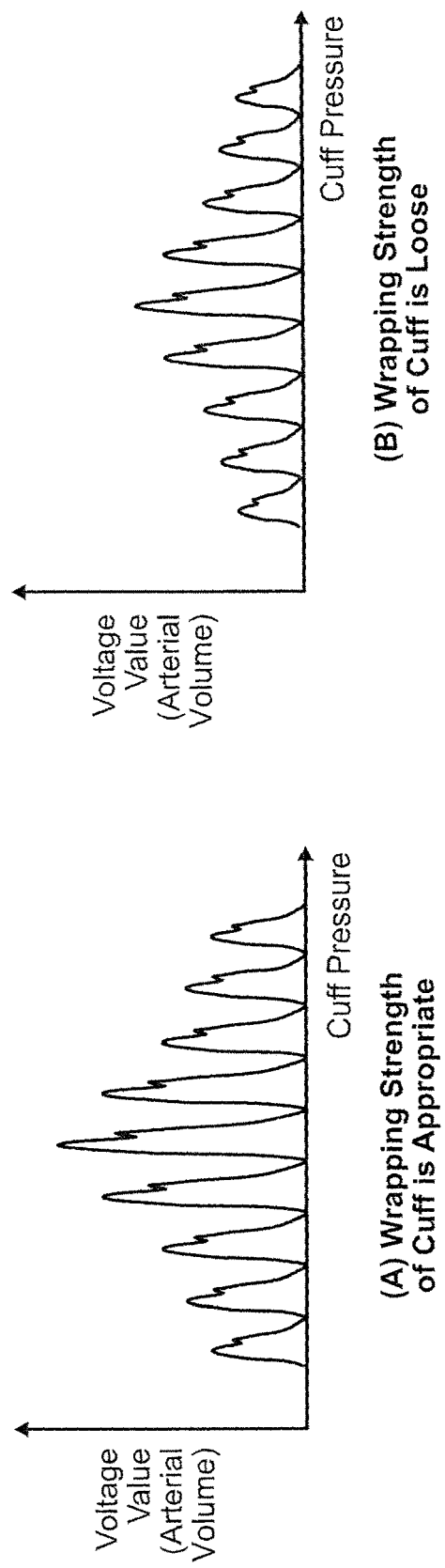
FIG. 13 is a diagram showing an exemplary voltage value output from an artery volume detection circuit in the sphygmomanometer of FIG. 11.

(A) of FIG. 13 shows the change in the voltage signal (voltage value) output by the arterial volume detection circuit 74 following a change in cuff pressure in the case where the wrapping strength of the cuff 150 is appropriate. (B) of FIG. 13 shows the change in the voltage signal (voltage value) output by the arterial volume detection circuit 74 following a change in cuff pressure in the case where the wrapping strength of the cuff 150 is loose.

Referring to (A) and (B) of FIG. 13, the voltage value output decreases overall when the cuff 150 is loosely wrapped.

Note that when the wrapping strength of the cuff 150 is tight, the voltage value output increases overall, as compared with the case where the wrapping strength is appropriate. When, however, the wrapping strength of the cuff 150 is so tight as to obstruct the flow of the blood in the blood vessels, the voltage value output deceases overall, as compared with the case where the wrapping strength is appropriate.

3-2. Wrapping Strength Evaluation

The wrapping strength evaluation in step S110 (see FIG. 6) by the evaluation unit 122P of the sphygmomanometer 100 of the present embodiment will be described.

The control unit 122 first reads a voltage value corresponding to the blood pressure value obtained with the current blood pressure measurement as a first value. The blood pressure value referred to here may be the systolic blood pressure value, the diastolic blood pressure value or the average blood pressure value, for example. The blood pressure value referred to here may also be the cuff pressure value when the output voltage takes its maximum.

Next, with regard to the blood pressure measurement to date, a voltage value stored in Table 2 in the memory unit 123B in association with the person being measured for whom information in the was input at step S30 in Table 1 is read as a second value.

Note that as for the value read here as the second value, in the case where a value corresponding to the systolic blood pressure value is read as the voltage value obtained with the current blood pressure measurement, the level of the voltage value similarly corresponding to the systolic blood pressure value is also read as the value of the blood pressure measurement to date. In the case where a value corresponding to the diastolic blood pressure value is read, the voltage value similarly corresponding to the diastolic blood pressure value is also read as the value of the blood pressure measurement to date. In the case where a value corresponding to the average blood pressure value is read, the voltage value similarly corresponding to the average blood pressure value is also read as a value of the blood pressure measurement to date.

Also, the value read as the second value is the voltage value corresponding to the systolic blood pressure value or the like, and may be the immediately previous measurement result for the person being measured for whom information was input at step S30, or may be a representative value such as the average value, minimum value or maximum value for a prescribed number (e.g., 5 times) of most recent measurement results.

The control unit 122 then calculates the difference between the first value and the second value (second value−first value), and evaluates the wrapping strength based on the value of this difference REF02. For example, the wrapping strength is evaluated as being appropriate if REF02 is less than or equal to "C", tight if REF02 exceeds "C", and loose if REF02 is less than "−C".

Also, wrapping strength may be evaluated across multiple levels. For example, an example will be described in which wrapping strength is evaluated across seven levels. The wrapping strength is evaluated as being appropriate if REF02 is less than or equal to "C1", slightly tight if REF02 exceeds "C1" and is less than or equal to "C2", tight if REF02 exceeds "C2" and is less than or equal to "C3", quite tight if REF02 exceeds "C3", slightly loose if REF02 is less than "−C1" but greater than or equal to "−C2", loose if REF02 is less than "−C2" but greater than or equal to "−C3", and quite loose if REF02 is less than "−C3". Note that in this case C1 to C3 are positive numbers, where C1<C2<C3.

In the present embodiment described above, information related to the amount of arterial volume change, which is the detection amount for the index of blood pressure detected based on the output of a sensor, is constituted by a voltage value output from the arterial volume detection circuit 74 that is used to evaluate wrapping strength.

An evaluation unit according to one or more embodiments of the present invention is constituted by the evaluation unit 122P that evaluates the wrapping strength of the cuff 150, by comparing the voltage value in the current detection result with a voltage value stored as a history. Note that the evaluation unit 122P outputs the evaluation result to the display unit 114 as the evaluation display portion 40 in FIG. 7, for example.

According to the invention disclosed in the embodiments described above, the detection amount for the index of blood pressure is detected using information output from a sensor based on the behavior of the cuff when blood pressure measurement is performed, and wrapping strength of the cuff is evaluated as a result of the detection amount being compared with a detection amount stored as a history. The person being measured is thereby able to recognize whether there is variation in the wrapping strength, based on the evaluation result.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERAL LIST

40 Evaluation display unit
70 Photoelectric sensor
71 Light emitting element
72 Light receiving element
73 Light emitting element drive circuit
74 Arterial volume detection circuit
80 Microphone
100 Sphygmomanometer
110 Device main body
114 Display unit
115 Operation unit
115A Power switch
115B Measurement switch
115C Stop switch
115D User selection switch
115E Record call Switch
122 Control unit
122A Pulse wave signal detection unit
122B Blood pressure measurement unit
122C Sound detection unit
122D Blood pressure measurement unit
122E Arterial volume detection unit
122F Blood pressure measurement unit
122P Evaluation unit
123A, 123B Memory unit
124 Power supply unit
125 Oscillation circuit
126 Pump drive circuit
127 Valve drive circuit
129 Timer
131 Air system component for use in blood pressure measurement
132 Pressure sensor
134 Pump
135 Valve
140 Air tube
150 Cuff
151 Air bladder
200 Measurement site
400 Screen

The invention claimed is:

1. A blood pressure measurement device provided with a cuff that compresses a measurement site by being wrapped therearound, comprising:
    a sensor that detects a behavior of the cuff; and
    a control unit that detects a first detection amount for an index of blood pressure based on an output of the sensor,
    wherein the control unit measures blood pressure to obtain at least a systolic blood pressure value in each measurement based on the first detection amount for the index of blood pressure,
    wherein the blood pressure measurement device further comprises a storage unit that stores a second detection amount of at least one previous measurement detected by the control unit,
    wherein the control unit evaluates a wrapping strength of the cuff, by obtaining a difference between the first detection amount detected based on the output of the sensor in a current measurement and the second detection amount in the at least one previous measurement stored in the storage unit, and indicating that the blood pressure result obtained was from a wrapping strength that was loose or tight;
    wherein, when the difference between the first detection amount and the second detection amount is greater than the predetermined amount, the cuff is tight,
    wherein, when the difference between the first detection amount and the second detection amount is less than the negative of the predetermined amount, the cuff is loose,
    wherein, when the difference between the first detection amount and the second detection amount is less than or equal to the predetermined amount, the cuff is appropriate,
    wherein the control unit is a processor that is specifically programmed to: detect the first detection amount for the index of blood pressure based on the output of the sensor; measure at least the systolic blood pressure value based on the first detection amount; and evaluate the wrapping strength of the cuff,
    wherein the first detection amount used for obtaining the difference is an amount related to an amount of arterial volume change in the measurement site around which the cuff is wrapped,
    wherein the amount of arterial volume change is a voltage output of the sensor, and
    wherein the second detection amount in the at least one previous measurement stored in the storage unit used for obtaining the difference corresponds to a representative value of measured blood pressure values based on each second detection amount of the at least one previous measurement stored in the storage unit.

2. The blood pressure measurement device according to claim 1, wherein the storage unit stores the detection amount of the at least one previous measurement in association with a history of a blood pressure value measured based on the detection amount.

3. The blood pressure measurement device according to claim 1, wherein the current measurement and the at least one previous measurement are each pressure pulse wave amplitude values or voltage values.

4. A blood pressure measurement device provided with a cuff that compresses a measurement site by being wrapped therearound, comprising:
   a sensor that detects a behavior of the cuff; and
   a control unit that detects a first detection amount for an index of blood pressure based on an output of the sensor,
   wherein the control unit measures blood pressure to obtain at least a systolic blood pressure value in each measurement based on the first detection amount for the index of blood pressure,
   wherein the blood pressure measurement device further comprises a storage unit that stores a second detection amount of at least one previous measurement detected by the control unit,
   wherein the control unit evaluates a wrapping strength of the cuff, by obtaining a difference between the first detection amount detected based on the output of the sensor in a current measurement and the second detection amount in the at least one previous measurement stored in the storage unit, and indicating that the blood pressure result obtained was from a wrapping strength that was loose or tight;
   wherein, when the difference between the first detection amount and the second detection amount is greater than the predetermined amount, the cuff is tight,
   wherein, when the difference between the first detection amount and the second detection amount is less than the negative of the predetermined amount, the cuff is loose,
   wherein, when the difference between the first detection amount and the second detection amount is less than or equal to the predetermined amount, the cuff is appropriate,
   wherein the control unit is a processor that is specifically programmed to: detect the first detection amount for the index of blood pressure based on the output of the sensor; measure at least the systolic blood pressure value based on the first detection amount; and evaluate the wrapping strength of the cuff,
   wherein the first detection amount used for obtaining the difference is an amount related to an amount of arterial volume change in the measurement site around which the cuff is wrapped,
   wherein the amount of arterial volume change is a voltage output of the sensor,
   wherein the first detection amount for the index of blood pressure used for obtaining the difference is a cuff pressure when the output of the sensor takes its maximum value, and
   wherein the second detection amount in the at least one previous measurement stored in the storage unit used for obtaining the difference corresponds to a maximum value of a prescribed number of most recent measurement results.

5. A blood pressure measurement device provided with a cuff that compresses a measurement site by being wrapped therearound, comprising:
   a sensor that detects a behavior of the cuff; and
   a control unit that detects a first detection amount for an index of blood pressure based on an output of the sensor,
   wherein the control unit measures blood pressure to obtain at least a systolic blood pressure value in each measurement based on the first detection amount for the index of blood pressure,
   wherein the blood pressure measurement device further comprises a storage unit that stores a second detection amount of at least one previous measurement detected by the control unit,
   wherein the control unit evaluates a wrapping strength of the cuff, by obtaining a difference between the first detection amount detected based on the output of the sensor in a current measurement and the second detection amount in the at least one previous measurement stored in the storage unit, and indicating that the blood pressure result obtained was from a wrapping strength that was loose or tight;
   wherein, when the difference between the first detection amount and the second detection amount is greater than the predetermined amount, the cuff is tight,
   wherein, when the difference between the first detection amount and the second detection amount is less than the negative of the predetermined amount, the cuff is loose,
   wherein, when the difference between the first detection amount and the second detection amount is less than or equal to the predetermined amount, the cuff is appropriate,
   wherein the control unit is a processor that is specifically programmed to: detect the first detection amount for the index of blood pressure based on the output of the sensor; measure at least the systolic blood pressure value based on the first detection amount; and evaluate the wrapping strength of the cuff,
   wherein the first detection amount used for obtaining the difference is an amount related to an amount of arterial volume change in the measurement site around which the cuff is wrapped,
   wherein the amount of arterial volume change is a voltage output of the sensor, and
   wherein the second detection amount in the at least one previous measurement stored in the storage unit used for obtaining the difference corresponds to at least one blood pressure value selected from the group consisting of: a systolic blood pressure, an average blood pressure, and a diastolic blood pressure based on each second detection amount of the at least one previous measurement stored in the storage unit.

6. A blood pressure measurement device provided with a cuff that compresses a measurement site by being wrapped therearound, comprising:
   a sensor that detects a behavior of the cuff; and
   a control unit that detects a detection amount for an index of blood pressure based on an output of the sensor,
   wherein the control unit measures blood pressure to obtain at least a systolic blood pressure value in each measurement based on the detection amount,
   wherein the blood pressure measurement device further comprises a storage unit that stores a detection amount of at least one previous measurement detected by the control unit,
   wherein the control unit evaluates a wrapping strength of the cuff, by obtaining a difference between the detection amount detected based on the output of the sensor in a current measurement and the detection amount in the at least one previous measurement stored in the storage unit, and indicating that the blood pressure result obtained was from a wrapping strength that was loose or tight;

wherein, when the difference between the first detection amount and the second detection amount is greater than the predetermined amount, the cuff is tight, wherein, when the difference between the first detection amount and the second detection amount is less than the negative of the predetermined amount, the cuff is loose, wherein, when the difference between the first detection amount and the second detection amount is less than or equal to the predetermined amount, the cuff is appropriate, wherein the control unit is a processor that is specifically programmed to: detect the detection amount for the index of blood pressure based on the output of the sensor; measure at least the systolic blood pressure value based on the detection amount; and evaluate the wrapping strength of the cuff, and wherein the detection amount is a volume of Korotkoff sounds of an artery in the measurement site around which the cuff is wrapped based on the output of the sensor.

7. A wrapping strength detector, for detecting a variation in the wrapping strength of a cuff, for use in a blood pressure measurement device provided with the cuff that compresses a measurement site by being wrapped therearound, said detector comprising:

a sensor that detects a behavior of the cuff; and a control unit that detects a first detection amount based on an output of the sensor, wherein the wrapping strength detector further comprises a storage unit that stores a second detection amount of at least one previous measurement detected by the control unit, wherein the control unit evaluates a wrapping strength of the cuff, by obtaining a difference between the first detection amount detected based on the output of the sensor in a current measurement and the second detection amount in the at least one previous measurement stored in the storage unit, and indicating that the blood pressure result obtained was from a wrapping strength that was loose or tight;

wherein, when the difference between the first detection amount and the second detection amount is greater than the predetermined amount, the cuff is tight, wherein, when the difference between the first detection amount and the second detection amount is less than the negative of the predetermined amount, the cuff is loose, wherein, when the difference between the first detection amount and the second detection amount is less than or equal to the predetermined amount, the cuff is appropriate, wherein the control unit is a processor that is specifically programmed to: detect the first detection amount based on the output of the sensor; and evaluate the wrapping strength of the cuff, wherein the first detection amount used for obtaining the difference is an amount related to an amount of arterial volume change in the measurement site around which the cuff is wrapped, wherein the amount of arterial volume change is a voltage output of the sensor, and wherein the second detection amount in the at least one previous measurement stored in the storage unit used for obtaining the difference corresponds to a representative value of measured blood pressure values based on each second detection amount of the at least one previous measurement stored in the storage unit.

* * * * *